United States Patent
Zhang et al.

(10) Patent No.: US 7,050,853 B2
(45) Date of Patent: May 23, 2006

(54) DETECTION OF PATIENT MORTALITY BY AN IMPLANTABLE MEDICAL DEVICE

(75) Inventors: Geng Zhang, Vadnais Heights, MN (US); Richard S. Sanders, Stillwater, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 127 days.

(21) Appl. No.: 10/614,677

(22) Filed: Jul. 7, 2003

(65) Prior Publication Data

US 2005/0010254 A1    Jan. 13, 2005

(51) Int. Cl.
*A61N 1/362* (2006.01)

(52) U.S. Cl. .......................................... 607/9; 600/509
(58) Field of Classification Search .................... 607/9, 607/6; 600/509, 513

See application file for complete search history.

(56) References Cited

U.S. PATENT DOCUMENTS

| | | | | |
|---|---|---|---|---|
| 4,223,678 A * | 9/1980 | Langer et al. | ................. | 607/5 |
| 4,763,646 A * | 8/1988 | Lekholm | ..................... | 607/14 |
| 5,190,035 A | 3/1993 | Salo et al. | | |
| 5,518,001 A * | 5/1996 | Snell | ......................... | 600/510 |
| 6,161,042 A | 12/2000 | Hartley et al. | | |
| 6,385,485 B1* | 5/2002 | Ripart | ......................... | 600/513 |
| 2003/0220582 A1* | 11/2003 | Zhu et al. | ................... | 600/549 |
| 2004/0122331 A1* | 6/2004 | Freeberg | ..................... | 600/510 |

* cited by examiner

Primary Examiner—Jeffrey R. Jastrzab
Assistant Examiner—Alyssa M. Alter
(74) Attorney, Agent, or Firm—Schwegman, Lundberg, Woessner & Kluth, P.A.

(57) ABSTRACT

An implantable cardiac rhythm management device is programmed and configured to detect a death event. When such an event is detected, the device ceases recording of physiological data, thus preserving in the device's memory the data collected at and shortly before the time of death. A death event may be detected by detecting of an absence of intrinsic electrical activity in the patient's heart and a lack of an evoked response to a predetermined number of pacing pulses.

20 Claims, 2 Drawing Sheets

DETECTION OF PATIENT MORTALITY BY AN IMPLANTABLE MEDICAL DEVICE

FIELD OF THE INVENTION

This invention pertains to systems and methods for cardiac rhythm management. In particular, the invention relates to cardiac pacemakers and their methods of operation.

BACKGROUND

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. The term "pacemaker" as used herein, however, should be taken to mean both pacemakers and any device with a pacing functionality, such as an implantable cardioverter/defibrillator with a pacemaker incorporated therein.

Implantable medical devices are typically configured to record physiological data from sensing channels such as cardiac electrograms. The data is stored in memory so that it can be later downloaded via a telemetry link and used for patient and/or device evaluation. Because an implantable device has a very limited data storage capacity, it is conventional for such devices to the record physiological data in a rolling fashion where older data is continuously overwritten by newer data. Upon the death of the patient in whom such a device is implanted, the device will continue to record blank data which overwrites the data collected shortly before the actual death event. Such data would be useful, however, to clinicians and forensic investigators in determining the cause of death.

SUMMARY

In accordance with the present invention, an implantable medical device is programmed and configured to detect a death event. When such an event is detected, the device is further programmed to cease recording of physiological data, thus preserving in the device's memory the data collected at and shortly before the time of death. One or more of the following criteria may be used to detect a death event: detection of an absence of intrinsic electrical activity in the patient's heart and a lack of an evoked response to a predetermined number of pacing pulses, detection of an absence of physical activity, detection of an absence of heart sounds, and detection of an absence of changes in transthoracic impedance.

DETAILED DESCRIPTION

Figure 1:
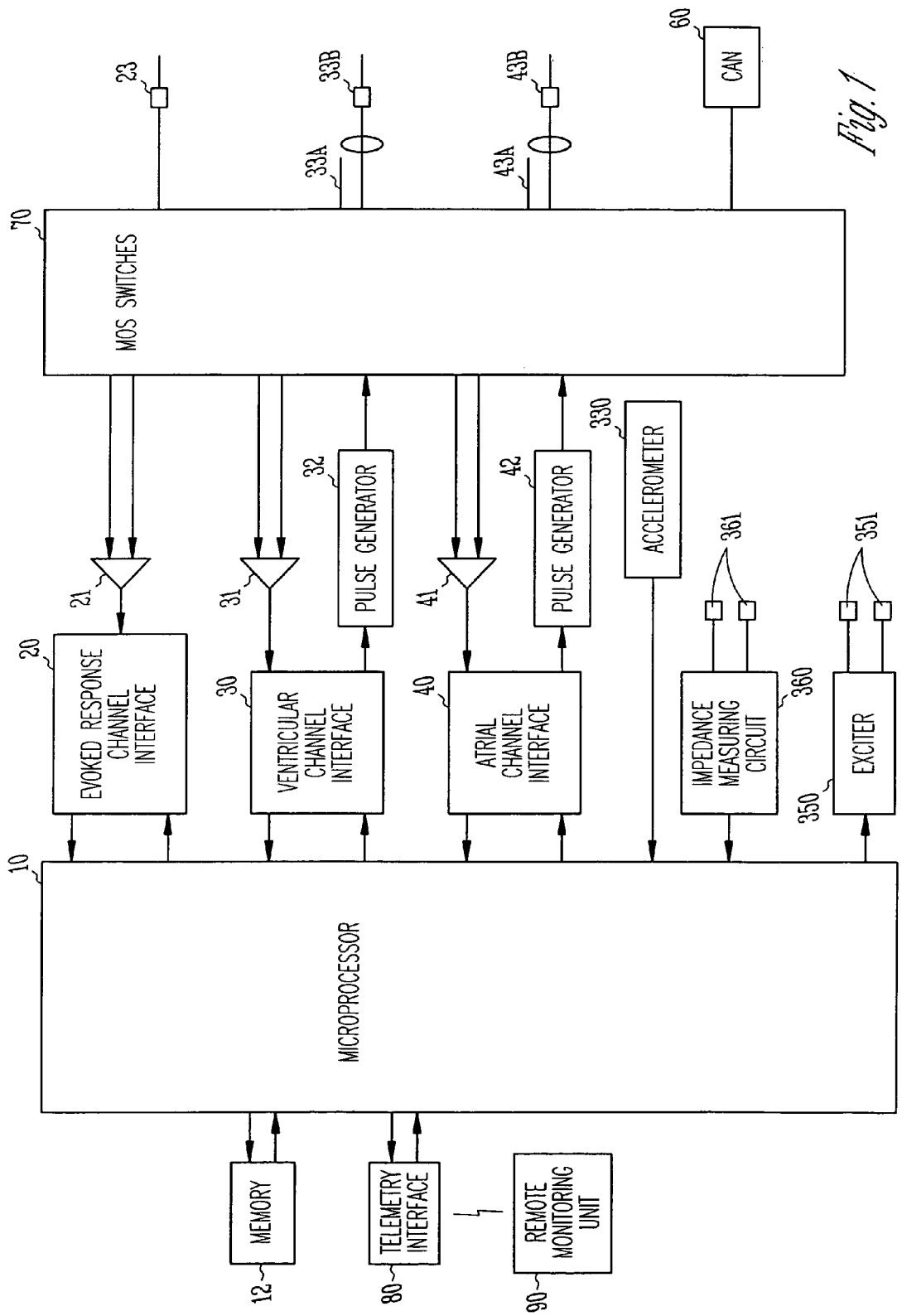
FIG. 1 is a block diagram of an exemplary cardiac rhythm management device.

Implantable cardiac rhythm management devices, such as ICDs and pacemakers, typically collect and record physiological data as part of their normal operation. A log of the collected data maintained by the device may include cardiac electrograms and possibly other types of signals recorded from the device's sensing channels as well as the time of occurrence of particular detected events. The log is stored in the device's memory so that it can be later downloaded to an external device such as an external programmer via a telemetry link. The information contained in the log can then be used by a clinician in evaluating the patient in whom the device is implanted and planning further treatment.

Because implantable devices have a limited data storage capacity, a data log such as described above is stored in a log buffer file in the device's memory that operates as a FIFO queue or similar data structure so that the oldest data contained in the buffer is overwritten with the most recent data. This is advantageous since it is usually the most recently recorded data that is of greatest significance for clinical evaluation purposes. One untoward side-effect of this device behavior, however, is that if the patient should die, the device may continue to collect blank data from its sensing channels and record the blank data in the log buffer file. The valid data in the buffer collected at and shortly before the lethal event is thus overwritten by the blank data and erased. This erased data, however, may be valuable in determining the circumstances of the patient's death and hence of use to both clinicians and forensic investigators. It would therefore be advantageous to preserve this information. In accordance with the present invention, an implantable device is programmed to recognize a death event from data collected by one or more sensory modalities with which the device is configured. Upon determining that the patient has died, the device then ceases all updating of the data in the log buffer, thus preserving its contents for future evaluation.

One well-known characteristic of death is the absence of intrinsic electrical activity in the heart (i.e., spontaneous heart beats). Thus, a device could determine that a death event has occurred and stop the further recording of data if no intrinsic beats are detected for a predetermined length of time. A device with a pacing functionality, however, may normally deliver pacing pulses at a pacing rate that is above the patient's intrinsic heart rate so that intrinsic beats are suppressed. Such overdrive suppression of intrinsic heart beats may occur with either asynchronous pacing at a fixed rate or with demand pacing where paces are delivered to the heart only when the intrinsic rate falls below a predetermined rate (i.e., the lower rate limit or LRL setting of the device). Thus, in the situation where the device paces the heart and may not expect to sense intrinsic activity, the absence of detected intrinsic activity cannot be used as the sole criterion for determining death.

A pacing pulse delivered to a pacing site causes a cardiac contraction by eliciting a traveling wave of depolarization in the myocardium, referred to as an evoked response, which then excites the rest of the heart. Pacemakers may be configured to detect the evoked response resulting from a pacing pulse in order to verify that the pacing pulse has captured the heart. Detection of an evoked response may also be used as a criterion for determining death. When death occurs and the heart stops beating, heart cells are deprived of blood and oxygen, thus ceasing their cellular metabolism. Energy derived from cellular metabolism is necessary in order to maintain the ionic concentration gradients responsible for the electrical excitability of heart cells. This means that very shortly after the patient has died, a pacing pulse delivered to the heart no longer elicits an evoked response. A device with a pacing functionality may thus test for whether death has occurred by determining if an evoked response has failed to occur during some predetermined number of consecutive paces and if an absence of intrinsic electrical activity is also detected.

Failure to detect intrinsic cardiac activity and/or evoked responses to pacing pulses, however, may be due to a hardware malfunction (e.g., lead breakage or electronic component failure) rather than a death event. If no intrinsic activity and no evoked responses are detected, the device may therefore be further programmed to require sensing of a pacing artifact before declaring a death event. The device may also be programmed to make use of other sensing modalities available to it for determining death, either in addition to, or instead of, the aforementioned criterion based upon a lack of intrinsic electrical activity and evoked responses to paces. For example, pacemakers may be configured with an impedance sensor for measuring cardiac stroke volume and/or minute ventilation, the latter parameter being used for rate-adaptive pacing. The sensor functions by measuring the transthoracic impedance which changes in accordance with the movement of air into and out of the lungs and with the movement of blood into and out of the heart. Since both of these phenomena cease post-mortem, another criterion which the device may be programmed to use for detecting a death event is a lack of changes in transthoracic impedance for some predetermined length of time. Pacemakers may also be configured with an accelerometer which is normally used for sensing body activity in order to control rate-adaptive pacing. Cessation of body activity, which may follow a sudden spike in activity, may be a useful criterion for detecting death. The accelerometer may also be used for detecting heart sounds which result from valve closures as the heart beats. Thus, another criterion that the device may use for detecting death is a lack of detected heart sounds for some predetermined length of time.

1. Exemplary Hardware Description

Pacemakers are typically implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

The present invention may be incorporated into a number of different implantable medical devices. For illustrative purposes, however, a block diagram of a dual-chamber pacemaker (i.e., one that sense and/or paces the atria and ventricles) is shown in FIG. 1. The controller of the pacemaker is made up of a microprocessor 10 communicating with a memory 12, where the memory 12 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals.

Programming of the device after implantation is performed using a telemetry interface 80 by which the device may wirelessly communicate with an external programmer. Data generated by the device may also be downloaded to the external programmer or other device with the telemetry link.

The device has an atrial sensing/pacing channel comprising ring electrode 43a, tip electrode 43b, sense amplifier 41, pulse generator 42, and an atrial channel interface 40 which communicates bidirectionally with a port of microprocessor 10. The device also has a ventricular sensing/pacing channel that includes ring electrodes 33a, tip electrodes 33b, sense amplifier 31, pulse generator 32, and a ventricular channel interface 30. For each channel, the electrodes are connected to the pacemaker by a lead and used for both sensing and pacing. A MOS switching network 70 controlled by the microprocessor is used to switch the electrodes from the input of a sense amplifier to the output of a pulse generator.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or changing the pacing pulse amplitude. The microprocessor 10 controls the overall operation of the device in accordance with programmed instructions stored in memory. The sensing circuitry of the pacemaker generates atrial and ventricular sense signals when voltages sensed by the electrodes exceed a specified threshold. The controller then interprets sense signals from the sensing channels and controls the delivery of paces in accordance with a programmed pacing mode. The sense signals from any of the sensing channels of the pacemaker in FIG. 1 can be digitized and recorded by the controller to constitute an electrogram that can either be transmitted via the telemetry link to an external programmer or stored for later transmission.

The device is also equipped with an evoked response sensing channel that comprises an evoked response channel interface 20 and a sense amplifier 21 that has its differential inputs connected to a unipolar electrode 23 and to the device housing or can 60 through the switching network 70. Evoked response sensing may be used to verify that a pacing pulse has achieved capture of the heart and caused a contraction or, as explained above, used in detecting a death event. Other embodiments may employ the same channel used to sense intrinsic activity and control pacing as an evoked response sensing channel. Sensing channels in a pacemaker that provide senses for controlling pacing are commonly rendered refractory (i.e., insensitive) for a specified time period immediately following a pace in order to prevent the pacemaker from mistaking a pacing pulse or afterpotential for an intrinsic beat. This is done by the pacemaker controller ignoring sensed events during the refractory intervals, which are defined for both atrial and ventricular sensing channels and with respect to both atrial and ventricular pacing events. Furthermore, a separate period that overlaps the early part of a refractory interval is also defined, called a blanking interval during which the sense amplifiers are blocked from receiving input in order to prevent their saturation during a pacing pulse. If the same sensing channel is used for both sensing intrinsic activity to control pacing and for sensing an evoked response, a period for sensing an evoked response should preferably be defined that supercedes any normal refractory period of the sensing channel.

An accelerometer 330 enables the controller to measure body motion and may be used to adapt the pacing rate in accordance with changes in the patient's physical activity.

The accelerometer 330 or a similar microphonic device may also be used to detect heart sounds. When the heart beats, closure of valves brought about by pressure differentials in the heart are associated with audible heart sounds that can be heard by auscultation with a stethoscope. The first heart sound, designated S1, results when the AV valves (the mitral and tricuspid valves) close at the beginning of systole as the ventricular contraction causes a sudden backflow of blood toward the atria and against the valves. Due to the elastic nature of the valves, the movement of blood toward the atria causes the valves to bulge toward the atria and then recoil blood back toward the ventricle. This causes a period of reverberation that results in vibrations being transmitted through the blood and body tissues. The second heart sound, designated S2, similarly results when the semilunar valves (the aortic and pulmonary valves) close at the end of systole as the ventricular pressure drops. When the mechanical pumping action of the heart ceases, no heart sounds are detected by the accelerometer, and this may be used by the device as a criterion for detecting death.

Also interfaced to the controller is an exciter 350 and an impedance measuring circuit 360. The exciter supplies excitation current of a specified amplitude (e.g., as a pulse waveform with constant amplitude) to excitation electrodes 351 that are disposed in the thorax. Voltage sense electrodes are disposed in a selected region of the thorax so that the potential difference between the electrodes while excitation current is supplied is representative of the transthoracic impedance between the voltage sense electrodes. The impedance measuring circuitry 360 processes the voltage sense signal from the voltage sense electrodes 361 to derive the impedance signal. The conductive housing or can may be used as one of the voltage sense electrodes. Further processing of the impedance signal allows the derivation of signal representing respiratory activity and/or cardiac blood volume, depending upon the location the voltage sense electrodes in the thorax. (See, e.g., U.S. Pat. Nos. 5,190,035 and 6,161,042, assigned to the assignee of the present invention and hereby incorporated by reference.) If the impedance signal is filtered to remove the respiratory component, the result is a signal that is representative of blood volume in the heart at any point in time. As explained above, the absence of detected changes in transthoracic impedance may be used as a criterion for detecting death.

2. Exemplary Algorithm for Death Detection

Figure 2:
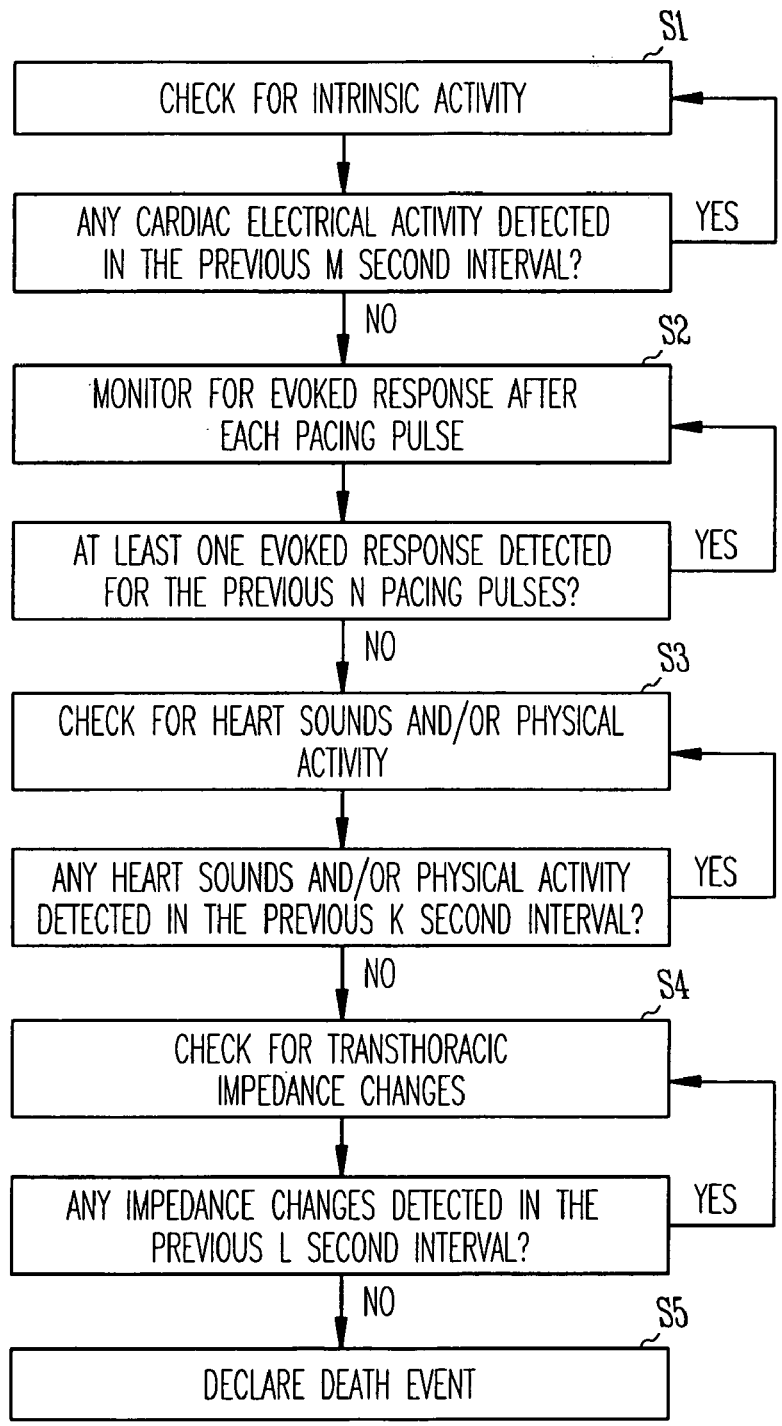
FIG. 2 illustrates an exemplary algorithm by which an implantable device may detect the death of the patient.

FIG. 2 illustrates an exemplary algorithm that a device such as depicted in FIG. 1 may use to detect the death of the patient as implemented by appropriate programming of the controller. At step S1, the device checks for intrinsic cardiac electrical activity. If no cardiac electrical activity has been detected in the previous M second interval, the device next monitors the evoked responses to delivered pacing pulses at step S2. As long as at least one evoked response is detected in the previous N pacing pulses, the monitoring continues. If no evoked responses are detected, the device next checks for the presence of heart sounds and/or physical activity at step S3. If no heart sounds and/or physical activity have been detected in the previous K second interval, the device then checks for transthoracic impedance changes at step S4. If no impedance changes have been detected in the previous L second interval, the device declares a death event at step S5 and ceases any further recording of physiological data. It should be understood that other embodiments of the invention may not include all of the criteria shown in the FIG. 2 for detecting a death event or may include additional criteria as discussed above. For example, the device may be programmed to detect a death event if no intrinsic activity was detected in the previous M second interval and if no evoked responses have been detected in the previous N pacing pulses. Other embodiments may then require that one or more additional criteria be met before a death event is detected such as: 1) no transthoracic impedance changes have been detected in the previous L second interval, 2) no physical activity has been detected in a previous J second interval, 3) no physical activity has been detected in a previous J second interval and the J second interval is preceded by a detection of a sudden increase in activity level, 4) no heart sounds have been detected in a previous K second interval, 5) detection of a pacing artifact when a pace is delivered, 6) an episode of atrial fibrillation precedes the detection of no intrinsic activity and no evoked responses to paces, and 7) an episode of ventricular fibrillation precedes the detection of no intrinsic activity and no evoked responses to paces.

3. Alarm Function After Death Detection

As described above, one of the benefits of providing an implantable medical device with the capability of detecting the death of the patient is that the device's data logs may be preserved for subsequent analysis. Detection of patient death by the device may also be used to trigger an alarm function. In this embodiment a remote monitoring unit 90 with the capability of communicating over a network connection (e.g., using a phone line or internet connection) is configured to communicate with the implantable device over the wireless telemetry link. The remote monitoring unit is designed to be placed in the patient's home or other location so as to be able to communicate with the implantable device. This enables the remote monitoring unit to send information to and/or receive information from the implantable device and retransmit the information to some central location via the network connection. The remote monitoring unit may be configured to periodically interrogate the implantable device as to the patient's status and/or receive messages autonomously generated by the implantable device. In either case, upon detection of patient death by the implantable device and transmission of a message signifying the event to the remote monitoring unit, an alarm function may be triggered in the remote monitoring unit whereby appropriate personnel are alerted to the situation over the network connection.

It may also be desirable for the outputs of a cardiac rhythm management device (i.e., pacing pulses and shock pulses) to be turned off after a death event in order to prevent potential damage from occurring during post-mortem processing. Accordingly, the implantable device may be programmed to automatically turn off such outputs upon detection of a death event. Alternatively, the remote monitoring unit may issue a command for the implantable device to turn off its outputs upon detection of a death event, where the command may either be generated automatically by the remote monitoring unit or by personnel in communication therewith over the network connection.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
one or more sensing channels for sensing intrinsic cardiac activity and for sensing evoked responses to paces;

a pacing channel for delivering paces to a cardiac chamber;

a controller for delivering paces to the cardiac chamber in accordance with a programmed pacing mode, the controller including a memory for program and data storage;

wherein the controller is programmed to record physiological data from a sensing channel in memory such that older data is overwritten by newer data;

wherein the controller is programmed to detect a death event if no intrinsic cardiac activity has been detected in a previous M second interval, if no evoked responses to paces have been detected for the previous N delivered paces, and if a pacing artifact is detected when a pace is delivered; and, wherein the controller is programmed to cease recording of physiological data upon detection of a death event.

2. The device of claim 1 further comprising an impedance sensor and wherein the controller is further programmed to detect a death event only if no changes in transthoracic impedance have been detected in a previous L second interval.

3. The device of claim 1 further comprising an accelerometer and wherein the controller is further programmed to detect a death event only if no heart sounds have been detected in a previous K second interval.

4. The device of claim 1 further comprising an accelerometer and wherein the controller is further programmed to detect a death event only if no activity level has been detected in a previous J second interval.

5. The device of claim 1 further comprising an accelerometer and wherein the controller is further programmed to detect a death event only if no activity level has been detected in a previous J second interval and if the J second interval was preceded by a detection of a sudden increase in activity level.

6. The device of claim 1 wherein the controller is further programmed to detect a death event only if an episode of atrial fibrillation precedes the detection of no intrinsic activity and no evoked responses to paces.

7. The device of claim 1 wherein the controller is further programmed to detect a death event only if an episode of ventricular fibrillation precedes the detection of no intrinsic activity and no evoked responses to paces.

8. The device of claim 1 wherein the controller is further programmed to cease outputting pacing pulses upon detection of a death event.

9. The device of claim 1 wherein the controller is further programmed to communicate the detection of a death event to a remote monitoring unit.

10. A method for operating a cardiac rhythm management device, comprising:

sensing intrinsic cardiac activity and evoked responses to paces delivered to a cardiac chamber;

recording physiological data from a sensing channel in a memory such that older data is overwritten by newer data;

detecting a death event if no intrinsic cardiac activity has been detected in a previous M second interval, if no evoked responses to paces have been detected for the previous N delivered paces, and if a pacing artifact is detected when a pace is delivered; and, ceasing the recording of physiological data upon detection of a death event.

11. The method of claim 10 further comprising detecting a death event only if no changes in transthoracic impedance have been detected in a previous L second interval.

12. The method of claim 10 further comprising detecting a death event only if no heart sounds have been detected in a previous K second interval.

13. The method of claim 10 further comprising detecting a death event only if no activity level has been detected in a previous J second interval.

14. The method of claim 10 further comprising detecting a death event only if no activity level has been detected in a previous J second interval and if the J second interval was preceded by a detection of a sudden increase in activity level.

15. The method of claim 10 further comprising detecting a death event only if an episode of atrial fibrillation precedes the detection of no intrinsic activity and no evoked responses to paces.

16. The method of claim 10 further comprising detecting a death event only if an episode of ventricular fibrillation precedes the detection of no intrinsic activity and no evoked responses to paces.

17. The method of claim 10 further comprising ceasing the delivery of pacing pulses upon detection of a death event.

18. The method of claim 10 further comprising communicating the detection of a death event to a remote monitoring unit.

19. The method of claim 18 further comprising triggering an alarm in the remote monitoring unit which alerts appropriate personnel over a network connection.

20. The method of claim 18 further comprising ceasing the delivery of pacing pulses upon receipt of a command from the remote monitoring unit upon detection of a death event.

* * * * *